United States Patent
Macdonald et al.

(10) Patent No.: US 7,531,558 B2
(45) Date of Patent: May 12, 2009

(54) CARBOXAMIDE DERIVATIVES

(75) Inventors: Gregor James Macdonald, Harlow (GB); Darren Jason Mitchell, Harlow (GB); Harshad Kantilal Rami, Harlow (GB); Mervyn Thompson, Harlow (GB); Leontine Saskia Trouw, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 580 days.

(21) Appl. No.: 10/545,283

(22) PCT Filed: Feb. 12, 2004

(86) PCT No.: PCT/GB2004/000543

§ 371 (c)(1),
(2), (4) Date: Aug. 11, 2005

(87) PCT Pub. No.: WO2004/072069

PCT Pub. Date: Aug. 26, 2004

(65) Prior Publication Data

US 2006/0148855 A1    Jul. 6, 2006

(30) Foreign Application Priority Data

Feb. 14, 2003   (GB) ................... 0303464.2
Mar. 6, 2003    (GB) ................... 0305163.8

(51) Int. Cl.
*A61K 31/4436*   (2006.01)
*C07D 417/12*    (2006.01)

(52) U.S. Cl. .................. 514/338; 546/270.1
(58) Field of Classification Search .......... 546/270.1; 514/338
See application file for complete search history.

(56) References Cited

U.S. PATENT DOCUMENTS

2006/0100245 A1 * 5/2006 Bakthavatchalam et al. . 514/332

FOREIGN PATENT DOCUMENTS

| WO | WO 0027819 | 5/2000 |
| WO | WO 0069849 | 11/2000 |
| WO | WO 0208221 | 1/2002 |
| WO | WO 02076946 | 10/2002 |

OTHER PUBLICATIONS

Vippagunta et al., "Crystalline Solid", Advanced Drug Delivery Reviews 48 (2001) 3-26.*
Guillory (in Brittain ed), "Polymorphism, etc.," NY: Marcel Dekker, Inc., 1999, 1-2, 183-226.*
Database Chemcats "online", Chemical Library, Nov. 15, 2001, Database accession No. 2000.949382 XP002280691.
Janusz, John , et al., "Vanilloids-Analogues of Capsaicin with antinociceptive/antiinflamatory activity", J. Med. Chem., vol. 36, pp. 2595-2604, XP001008868, (1993).

* cited by examiner

*Primary Examiner*—Patricia L Morris
(74) *Attorney, Agent, or Firm*—Reid S. Willis; Charles M. Kinzig

(57) ABSTRACT

Compounds of formula (I),

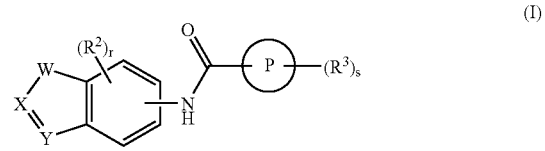

or a pharmaceutically acceptable salt or solvate thereof, wherein P, W, X, Y, $R^2$, $R^3$, r and s are as defined in the specification, processes for preparing such compounds, pharmaceutical compositions comprising such compounds and their use in therapy.

2 Claims, No Drawings

CARBOXAMIDE DERIVATIVES

This invention relates to novel amide derivatives having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Numbers WO 92/09285, WO 02/100819 and WO 02/076946. Particularly notable examples of Vanilloid compounds or Vanilloid receptor modulators are capsaicin or trans 8-methyl-N-vanillyl-6-nonenamide which is isolated from the pepper plant, capsazepine (*Tetrahedron*, 53, 1997, 4791) and olvanil or N-(4-hydroxy-3-methoxybenzyl)oleamide (*J. Med. Chem.*, 36, 1993, 2595).

International Patent Application, Publication Number WO 02/08221 discloses diaryl piperazine derivatives which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Number WO 03/068749 (published after the priority date of the present application) discloses carboxamide derivatives as Vanilloid receptor modulators and their use for the treatment of chronic and acute pain conditions.

According to a first aspect of the present invention, there is provided a compound of formula (I),

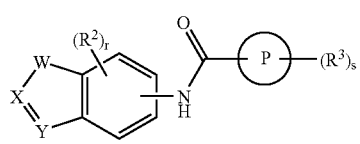

(I)

or a pharmaceutically acceptable salt or solvate thereof, wherein,

P is aryl, heteroaryl, heterocyclyl or cycloalkyl;

W, X and Y form a 5-membered nitrogen containing heteroaromatic ring wherein W, X and Y may be selected from $CR^{1a}$, $NR^{1b}$, N, S and O;

$R^{1a}$ and $R^{1b}$ independently are —H, alkyl, cycloalkyl, cycloalkylalkyl, aryl, arylalkyl, aryloxyalkyl, —$(CH_2)_xOR^4$ or —$(CH_2)_xNR^4R^5$;

$R^2$ is —H, alkyl, alkoxy or halo;

$R^{2a}$ is alkyl, alkoxy, halo or $CF_3$;

$R^{2b}$ is alkyl, alkoxy, halo or $CF_3$;

$R^3$ is —H, halo, alkyl, alkoxy, cycloalkyl, or aryl wherein said aryl group may be optionally substituted by one or more groups $R^{2a}$; heteroaryl wherein said heteroaryl group may be optionally substituted by one or more groups $R^{2b}$; aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$O(CH_2)_xOR^4$—$C(O)CF_3$, —C(O)alkyl, —C(O)cycloalkyl, —C(O)aralkyl, —C(O)Ar, —$C(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)R^6$, —$(CH_2)_xOR^6$, —$(CH_2)_xNR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, -ZAr, —$(CH_2)_xS(O)_2R^6$, —$(OCH_2)_xS(O)_2R^6$, —$O(CH_2)_xS(O)_2R^6$, —$N(R^4)S(O)_2R^6$, —$N(R^4)C(O)R^6$ or —$(CH_2)_xC(O)$alkyl;

$R^4$ and $R^5$ may be the same or different and represent —H or alkyl or $R^4$ and $R^5$ together with the nitrogen atom to which they are attached form a heterocyclic ring;

$R^6$ is —H, alkyl or aryl;

$R^7$ is —H, alkyl or aryl;

Ar is aryl or heteroaryl;

m is 0, 1 or 2;

r is 0, 1, 2 or 3;

s is 0, 1, 2, 3, 4, 5 or 6;

x is 0, 1, 2, 3, 4, 5 or 6; and

Z is a bond, O, S, $NR^7$ or $CH_2$.

The invention embraces compounds represented by the formula (I) given above and tautomers thereof.

Preferably P is phenyl, pyridyl (eg pyrid-3-yl), pyrimidinyl (eg pyrimidin-5-yl), piperazinyl (eg piperazin-1-yl) or cyclohexyl; more preferably pyridyl e.g. pyrid-3-yl.

The 5-membered nitrogen containing heteroaromatic ring formed from W, X and Y and the phenyl ring to which it is fused preferably form a benzothiazole, benzotriazole, benzimidazole or indazole group. Further examples include benzisoxazole and benzoxazole.

Preferably $R^{1a}$ is —H or alkyl, particularly $R_{1a}$ is —H or methyl especially methyl.

Preferably $R^{1b}$ is —H or alkyl, particularly $R^1$ is —H or methyl especially —H.

Preferably $R^2$ is alkyl (eg $CF_3$), alkoxy or halo.

Specific examples of W—X═Y include S-CMe═N, S—CH═N, NH—CH═N, NMe-CH═N, NH—N═CH, NH—N═N and NMe-N═CH.

Preferably $R^{2a}$ represents halo eg fluoro or chloro especially fluoro.

Preferably $R^{2b}$ represents alkyl (eg methyl).

Preferably $R^3$ is halo, alkyl, aryl e.g. phenyl, wherein said aryl group may be optionally substituted by one or more halo atoms e.g. fluoro or chloro, or heteroaryl e.g. pyridyl or pyrazolyl wherein said heteroaryl group may be optionally substituted by alkyl e.g. methyl. More preferably one of $R^3$ is phenyl optionally substituted by one or more halo atoms or heteroaryl optionally substituted by alkyl Preferably $R^4$ represents methyl or hydrogen.

Preferably $R^5$ represents methyl or hydrogen.

Preferably $R^6$ represents methyl.

Preferably $R^7$ is —H or alkyl especially —H or methyl.

Preferably r is 0, 1 or 2, more preferably r is 0 or 1, particularly r is 0.

Preferably s is 1 or 2. When s is 1, $R^3$ is preferably phenyl optionally substituted by one or more halo atoms or heteroaryl optionally substituted by alkyl. When s is 2, one $R^3$ is preferably phenyl optionally substituted by one or more halo atoms or heteroaryl optionally substituted by alkyl and the other is preferably alkyl e.g. methyl.

Preferably x is 0, 1, 2 or 3, especially 1, 2 or 3.

When P represents piperazin-1-yl substituted on the 4-position by aryl or heteroaryl, then preferably W—X═Y does not represent $NR^1$—$CR^1$═N or O—N═$CR^1$.

Compounds according to this invention include Examples 1-18 or pharmaceutically acceptable salts or solvates thereof.

A group of compounds which may be mentioned are those of formula (IA),

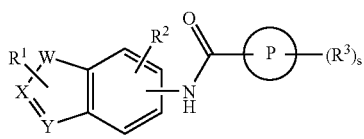

(IA)

or a pharmaceutically acceptable salt or solvate thereof, wherein,

P is aryl or heteroaryl;

$R^1$ represents —H, alkyl, cycloalkyl, cycloalkylalkyl, aryl, arylalkyl, aryloxyalkyl, —$(CH_2)_xOR^4$ or —$(CH_2)_xNR^4R^5$;

$R^2$ represents —H, alkyl, alkoxy or halo;

$R^3$ represents —H, halo, alkyl, alkoxy, cycloalkyl, aryl wherein said aryl group may be optionally substituted by one or more halo atoms; aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$O(CH_2)_xOR^4$, —$C(O)CF_3$, —C(O)alkyl, —C(O)cycloalkyl, —C(O)aralkyl, —C(O)Ar, —$C(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)R^6$, —$(CH_2)_xOR^6$, —$(CH_2)_xNR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, -ZAr, —$(CH_2)_xS(O)_2R^6$, —$(OCH_2)_xS(O)_2R^6$, —$N(R^4)S(O)_2R^6$, —$N(R^4)C(O)R^6$ or —$(CH_2)_xC(O)$alkyl;

$R^4$ and $R^5$ may be the same or different and represent —H or alkyl or $R^4$ and $R^5$ together with the nitrogen atom to which they are attached form a heterocyclic ring;

$R^6$ represents —H, alkyl or aryl;

$R^7$ represents —H or methyl;

Ar represents aryl or heteroaryl;

x represents an integer 0, 1, 2, 3, 4, 5 or 6;

m is 0, 1 or 2;

W, X and Y form a 5-membered nitrogen containing aromatic heterocyclic ring;

Z represents a bond, O, S, $NR^7$ or $CH_2$; and s is an integer value from 1 to 6.

In formula (IA):

Examples of the 5-membered nitrogen containing aromatic heterocyclic ring formed by W, X and Y (taken together with the phenyl ring) include benzotriazole, benzimidazole and indazole.

Suitably P represents phenyl or heteroaryl, more suitably phenyl or pyridyl, especially pyridyl, most especially pyrid-3-yl.

Suitably $R^1$ represents —H or alkyl, especially —H or methyl.

Suitably $R^2$ represents hydrogen.

Suitably, $R^3$ represents hydrogen, halo, alkyl, aryl wherein said aryl group may be optionally substituted by one or more halo atoms (e.g. fluoro); or —$O(CH_2)_xOR^4$, more suitably methyl or aryl (eg phenyl) optionally substituted by one or more halo atoms.

Suitably, s represents 1 or 2.

Suitably, x represents 0, 1, 2 or 3, especially 1, 2 or 3.

Suitably the 5-membered nitrogen containing aromatic heterocyclic ring formed by W, X and Y (taken together with the phenyl ring) is a benzimidazol-5-yl, benzimidazol-6-yl, benzotriazol-5-yl or indazol-6-yl group. Another example is indazol-5-yl.

Suitably $R^4$ represents methyl or hydrogen.

Suitably $R^5$ represents methyl or hydrogen.

Suitably $R^6$ represents methyl.

Suitably $R^7$ represents methyl or hydrogen.

Suitably Z represents a bond.

Suitably Ar represents phenyl.

Suitably the moiety —P—$(R^3)_s$ represents -2-methyl-6-(4-fluorophenyl)pyridin-3-yl (this numbering defining the pyridine nitrogen as position 1).

A further group of compounds which may be mentioned are those of formula (IB),

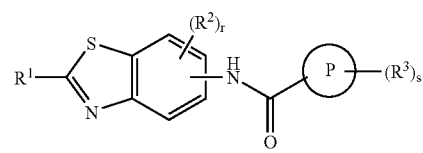

(IB)

or a pharmaceutically acceptable salt or solvate thereof, wherein,

P is aryl or heteroaryl;

$R^1$ is —H or alkyl;

$R^2$ is halo;

$R^3$ is halo, alkyl, alkoxy, cycloalkyl, aryl wherein said aryl group may be optionally substituted by one or more halo atoms; aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$O(CH_2)_xNR^4R^5$, —$O(CH_2)_xOR^4$, —$C(O)CF_3$, —C(O)alkyl, —C(O)cycloalkyl, —C(O)aralkyl, —C(O)Ar, —C(O)—$(CH_2)_xOR^4$, —C(O)—$(CH_2)_xNR^4R^5$, —C(O)alkoxy, —$C(O)NR^4R^5$, —$(CH_2)_xC(O)$alkoxy, —$(CH_2)_xOC(O)R^4$, —$(CH_2)_xOR^4$, —$(CH_2)_xNR^4R^5$, —$(CH_2)_xC(O)NR^4R^5$, —$(CH_2)_xN(R^4)C(O)R^4$, —$(CH_2)_xS(O)_2NR^4R^5$, —$(CH_2)_xN(R^4)S(O)_2R^6$, -ZAr, —$(CH_2)_xS(O)_mR^6$, —$O(CH_2)_xS(O)_mR^6$, —$N(R^4)S(O)_2R^6$, —$N(R^4)C(O)R^4$ or —$(CH_2)_xC(O)$alkyl;

$R^4$ and $R^5$ may be the same or different and represent —H, alkyl or aryl or $R^4$ and $R^5$ together with the nitrogen atom to which they are attached form a heterocyclic ring;

$R^6$ is alkyl or aryl;

$R^7$ is —H, alkyl or aryl;

Ar is aryl or heteroaryl;

x is 0, 1, 2, 3, 4, 5 or 6;

Z is a bond, O, S, $NR^7$ or $CH_2$;

m is 0, 1 or 2;

r is 0, 1 or 2; and s is an integer value from 1 to 6.

In formula (IB):

Suitably P is phenyl. Suitably, P is heteroaryl. More suitably, P is pyridyl e.g. 3-pyridyl.

Suitably $R^1$ is —H or methyl.

Suitably $R^3$ is halo, alkyl or aryl wherein said aryl group may be optionally substituted by one or more halo (eg fluoro) atoms.

Suitably m is 0.

Suitably x is 0, 1, 2 or 3, especially 1, 2 or 3.

Suitably r is 0.

Suitably s is 1 or 2.

The compounds of formula (IB) are preferably benzothiazol-5-yl derivatives.

Certain of the carbon atoms of formula (I) are chiral carbon atoms, and therefore compounds of formula (I) may exist as stereoisomers. The invention extends to all optical isomers such as stereoisomeric forms of the compounds of formula (I) including enantiomers and mixtures thereof, such as racemates. The different stereoisomeric forms may be separated or resolved one from the other by conventional methods or any given isomer may be obtained by conventional stereospecific or asymmetric syntheses.

As indicated above, the compounds of formula (I) can form salts, especially pharmaceutically acceptable salts. Suitable pharmaceutically acceptable salts are those used conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr$^n$"), iso-propyl ("Pr$^i$"), n-butyl ("Bu$^n$"), sec-butyl ("Bu$^s$"), tert-butyl ("Bu$^t$"), pentyl and hexyl. The term "cycloalkyl" as a group or part of a group refers to a saturated alicyclic hydrocarbon radical containing 3 to 12 carbon atoms, suitably 3 to 6 carbon atoms. Where appropriate, such alkyl groups may be substituted by one or more groups selected from halo (such as fluoro, chloro, bromo), —CN, —CF$_3$, —OH, —OCF$_3$, $C_{2-6}$ alkenyl, $C_{3-6}$ alkynyl, $C_{1-6}$ alkoxy, aryl and di-$C_{1-6}$ alkylamino. Alkyl groups are preferably unsubstituted or substituted by fluoro.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, iso-butoxy, sec-butoxy and tert-butoxy. Where appropriate, such alkoxy groups may be substituted by one or more groups selected from halo (such as fluoro, chloro, bromo), —CN, —CF$_3$, —OH, —OCF$_3$, $C_{1-6}$ alkyl, $C_{2-6}$ alkenyl, $C_{3-6}$ alkynyl, aryl and di-$C_{1-6}$ alkylamino. Alkoxy groups are preferably unsubstituted.

As used herein, the term "aryl" as a group or part of a group refers to a carbocyclic aromatic radical ("Ar"). Suitably such aryl groups are 5-6 membered monocyclic groups or 8-10 membered fused bicyclic groups, especially phenyl ("Ph"), biphenyl and naphthyl, particularly phenyl.

The term "naphthyl" is used herein to denote, unless otherwise stated, both naphth-1-yl and naphth-2-yl groups.

As used herein, the term "heteroaryl" as a group or part of a group refers to a stable 5-7-membered monocyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1. Examples of suitable heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolyl, carbazolyl, carbolinyl, chromanyl, chromenyl, cinnolinyl, decahydroquinolinyl, 2H, 6H-1,5,2-dithiazinyl, dihydrobenzofuranyl, furanyl, furazanyl, imidazolyl, 1H-indazolyl, indolinyl, indolyl, isobenzofuranyl, isochromanyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phthalazinyl, pteridinyl, purinyl, pyrazinyl, pyrazolyl, pyridooxazolyl, pyridoimidazolyl, pyridothiazolyl, pyridyl, pyrrolyl, quinazolinyl, quinolinyl, quinoxalinyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

The term "pyridyl" includes 2-pyridyl, 3-pyridyl and 4-pyridyl but preferably denotes 3-pyridyl.

Aryl and heteroaryl groups contained within the moieties $R^1$ and Ar may optionally be substituted with one or more substituents selected from the list consisting of halo, hydroxyl, carbonyl, alkoxy, alkyl, e.g. CF$_3$, NR$^4$R$^5$ and SO$_2$R$^6$ more suitably the list consisting of halo, hydroxyl, alkoxy, alkyl, e.g. CF$_3$, NR$^4$R$^5$ and SO$_2$R$^6$.

As used herein, the terms "heterocyclyl" and "heterocyclic" as a group or part of a group refer to stable heterocyclic non-aromatic single and fused rings containing one or more heteroatoms independently selected from nitrogen, oxygen and sulfur. A fused heterocyclyl ring system may include carbocyclic rings and need include only one heterocyclic ring. Examples of suitable heterocyclyl groups include, but are not limited to, piperazinyl, homopiperazinyl, piperidinyl, pyrrolidinyl and morpholinyl.

The term "halo" is used herein to describe, unless otherwise stated, a group selected from fluorine ("fluoro"), chlorine ("chloro"), bromine ("bromo") or iodine ("iodo").

The present invention also provides a process for the preparation of a compound of formula (I) or a pharmaceutically acceptable salt or solvate thereof, which process comprises:
(a) reacting a compound of formula (II),

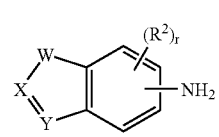

(II)

wherein, W, X, Y, $R^2$ and r are as defined in relation to formula (I), with a compound of formula (III),

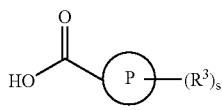

(III)

wherein, P, R³ and s are as defined in relation to formula (I) and thereafter, as necessary, carrying out one or more of the following reactions:
(i) converting one compound of formula (I) into another compound of formula (I);
(ii) removing any protecting group;
(iii) preparing a salt or a solvate of the compound so formed.

The reaction between a compound of formula (II) and a compound of formula (III) may be effected using conventional methods for the formation of an amide bond, such as those described in J March, *Advanced Organic Chemistry*, 4th edition, J Wiley & Sons, 1992, p. 419-421. Typically, the reaction may be carried out in a solvent such as dichloromethane, in the presence of a suitable diimide, such as 1-(3-dimethylaminopropyl)-3-ethylcarbodiimide hydrochloride. Alternatively a compound of formula (III) may be converted into the corresponding acyl chloride with a suitable chlorinating agent such as oxalyl chloride, followed by reaction with a compound of formula (II) in the presence of a suitable base such as pyridine in an inert solvent such as dichloromethane.

According to a further aspect of the present invention there is provided an an alternative process for the preparation of a compound of formula (I) where P is heterocyclyl (e.g. piperazinyl), or a pharmaceutically acceptable salt or solvate thereof, which process comprises reacting a compound of formula (II) with a compound of formula (IV):

(IV)

wherein, P is heterocyclyl and R³ and s are as defined in relation to formula (I); and thereafter, as necessary, carrying out one or more of the following reactions:
(i) converting one compound of formula (I) into another compound of formula (I);
(ii) removing any protecting group;
(iii) preparing a salt or a solvate of the compound so formed.

The reaction between a compound of formula (II) and a compound of formula (IV) may be effected using conventional methods for the formation of a urea derivative, for example, by treatment of a compound of formula (II) with a suitable activating reagent, such as phosgene, triphosgene, di-tertbutyl tricarbonate, or phenylchloroformate and a suitable base, followed by treatment with a compound of formula (IV). The reaction may be carried out in a suitable solvent such as dichloromethane. A suitable base is triethylamine.

Compounds of formula (II) are commercially available or may be prepared by the reaction of a compound of formula (V),

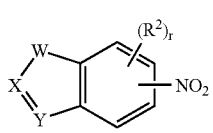

(V)

wherein, R² and r are as defined in relation to formula (I), with a suitable reducing agent.

The reaction of a compound of formula (V) with a reducing agent may be effected by methods well known in the art, such as those described in J March, *Advanced Organic Chemistry*, 4th edition, J Wiley & Sons, 1992, p. 1216-1218. Suitable reducing agents include (a) iron or zinc metal in hydrochloric acid, or (b) hydrogen in the presence of a suitable catalyst, such as, 5% palladium on charcoal. Reduction using hydrogen may conveniently be performed in a solvent such as methanol or ethanol.

Compounds of formula (V) are commercially available or may be prepared according to literature methods.

Compounds of formula (III) are commercially available or may be prepared according to a variety of known methods in accordance with the nature of the moiety, P. For example, compounds of formula (III) or their corresponding esters, where P is phenyl or heteroaryl may be prepared in accordance with methods described in J. Hassan et al., *Chem. Rev.*, 2002, 102, 1359. Hydrolysis of the corresponding ester compounds to compounds of formula (III) may be carried out in accordance with methods disclosed in J March, *Advanced Organic Chemistry*, 4th edition, J Wiley & Sons, 1992, p. 378-383. Compounds of formula (III) where P is heteroaryl may also be prepared in accordance with, for example, methods disclosed in the following references: H. Vorbruggen, *Adv. Het Chem.*, 1990, 49, 117 and E. Graf et al, *Synthesis*, 1999, 7, 1216.

The above-mentioned conversions of a compound of formula (I) into another compound of formula (I) include any conversion, which may be effected using conventional procedures, but in particular the said conversions include any combination of:
(i) converting one group $R^1$ into another group $R^1$;
(ii) converting one group $R^2$ into another group $R^2$; and
(iii) converting one group $R^3$ into another group $R^3$.

The above-mentioned conversions (i), (ii) and (iii) may be performed using any appropriate method under conditions determined by the particular groups chosen.

Suitable conversions of one group $R^1$ into another group $R^1$, as in conversion (i) above, include,
(a) converting a group $R^1$ which represents —H, into another group $R^1$ which represents alkyl, such as methyl. Such a conversion may be performed using an appropriate alkylation procedure, for example, by treating a compound of formula (I) wherein $R^1$ is —H with an agent, $R^1$-Z, where $R^1$ is alkyl and Z is halo, such as bromo, chloro or iodo, or —$OSO_2CF_3$.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures known in the art.

Pharmaceutically acceptable salts may be prepared conventionally by reaction with the appropriate acid or acid derivative.

Compounds of formula (I) and their pharmaceutically acceptable salts and solvates thereof have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular, in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which method comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which antagonism of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical adminstration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Abbreviations
'BuOH=tert-Butanol
DCM=Dichloromethane
DMF=N,N-Dimethylformamide
EtOAc=Ethyl acetate
MeOH=Methanol
$MgSO_4$=Magnesium sulfate
HCl=Hydrochloric acid Description 1 (D1)

3-Dimethylamino-4'-fluoropropiophenone hydrochloride

To a solution of 4'-fluoroacetophenone (5 g, 36.2 mmol) in propan-2-ol (90 ml) was added paraformaldehyde (4.35 g, 0.145 mol), dimethylamine hydrochloride (54.2 mmol) and concentrated HCl (0.8 ml). The reaction was heated at reflux for 18 h and on cooling the solvent was removed in vacuo. The residue was treated with acetone giving a white precipitate which was collected by filtration and dried in vacuo to give the title compound as a white solid (7.9 g). MS (ES): MH+ 196.

Description 2 (D2)

Ethyl 6-(4-fluorophenyl)-2-methyl nicotinate

A solution of 3-dimethylamino-4'-fluoropropiophenone hydrochloride (D1) (2.4 g, 9.3 mmol) and ethyl 3-aminocrotonate (1.74 ml, 13.8 mmol) in absolute ethanol (30 ml) was heated at reflux for 18 h. On cooling, the solvent was removed in vacuo to give an orange oil which was purified by column chromatography. Elution with 0-5% EtOAc/40-60 pet. ether gradient gave the title compound as a pale yellow solid (1.3 g). MS(ES): MH+ 260.

Description 3 (D3)

6-(4-Fluorophenyl)nicotinic acid

A solution of ethyl 6-(4-fluorophenyl)-2-methyl nicotinate (D2) (0.63 g, 2.4 mmol) in MeOH (12 ml) was treated with 2M sodium hydroxide (6 ml) for 18 h. The mixture was diluted with water and the methanol removed in vacuo. The aqueous residue was extracted with EtOAc then 20% $^t$BuOH/EtOAc and the combined organics were dried over $MgSO_4$ then concentrated in vacuo to give the title compound as a pale yellow solid (0.40 g). MS(ES): MH+ 232, M−H+ 230

Description 4 (D4)

6-(2,4-Difluorophenyl)nicotinic acid

The title compound was prepared from 2',4'-difluoroacetophenone using the procedures outlined for 6-(4-fluorophenyl)nicotinic acid (D1-D3).

Description 5 (D5)

6-(3,4-Difluorophenyl)nicotinic acid

The title compound was prepared from 3',4'-difluoroacetophenone using the procedures outlined for 6-(4-fluorophenyl)nicotinic acid (D1-D3).

Description 6 (D6)

6-(2,3-Difluorophenyl)nicotinic acid

The title compound was prepared from 2',3'-difluoroacetophenone using the procedures outlined for 6-(4-fluorophenyl)nicotinic acid (D1-D3).

Description 7 (D7)

2-Phenyl-5-pyrimidinecarboxylic acid

The title compound was prepared using a procedure similar to that outlined in P. Zhichkin, D. J. Fairfax & S. A. Eisenbeis, Synthesis 2002, 6, 720.

Description 8 (D8)

4-Methyl-2-phenyl-5-pyrimidinecarboxylic acid

The title compound was prepared using a procedure similar to that outlined in P. Schenone, L. Sansebastiano & L. Mosti, J. Heterocycl. Chem., 1990, 27, 295.

Description 9 (D9)

2-(4-Fluorophenyl)-4-methyl-5-pyrimidinecarboxylic acid

The title compound was prepared using a procedure similar to that outlined in P. Schenone, L. Sansebastiano & L. Mosti, J. Heterocycl. Chem., 1990, 27, 295 for the synthesis of D8.

Description 10 (D10)

4-(6-Methyl-2-pyridinyl)benzoic acid

The title compound was prepared using the procedure outlined in H. K. Rami, M. Thompson, G. J. Macdonald, S. M. Westaway & D. J. Mitchell, International Patent Application, Publication Number WO 03/068749.

Description 11 (D11)

5-Aminobenzothiazole

The title compound was prepared using the procedure outlined in T. L. Cupps et al, International Patent Application, Publication Number WO 98/23612.

Description 12 (D12)

6-Amino-1-methyl-1H-benzimidazole

The title compound was prepared using the procedure outlined in Y. T. Jeon et al, International Patent Application, Publication Number WO 96/04270.

The following compounds are commercially available:
5-Amino-2-methylbenzothiazole dihydrochloride
5-Amino-2-methylbenzothiazole
6-Amino-(1H)-benzimidazole
6-Aminoindazole
5-Aminobenzotriazole
4-(4-Chlorophenyl)-cyclohexane-1-carboxylic acid
4-(2-Fluorophenyl)piperazine
4-(2,4-Difluorophenyl)piperazine
5-Amino-1-methylindazole

EXAMPLE 1

6-(4-Fluorophenyl)-2-methyl-N-(2-methylbenzothiazol-5-yl)nicotinamide

5-Amino-2-methylbenzothiazole dihydrochloride (98 mg, 0.41 mmol), 6-(4-fluorophenyl)-2-methylnicotinic acid (D3) (96 mg, 0.42 mmol), 1-(3-dimethyl-aminopropyl)-3-ethyl-carbodiimide hydrochloride (119 mg, 0.62 mmol) and 4-dimethylaminopyridine (25 mg, 0.21 mmol) in DCM (2 ml) were stirred at room temperature overnight. The reaction mixture was purified directly by column chromatography, eluting with a 0-10% MeOH/DCM gradient to give the title compound as a white solid. $^1$H NMR (400 MHz, DMSO) δ (ppm): 8.42 (d, 1H), 8.21 (dd, 2H), 8.02 (d, 1H), 7.98 (d, 1H), 7.94 (d, 1H), 7.71 (dd, 1H), 7.34 (t, 2H), 2.80 (s, 3H), 2.67 (s, 3H). MS(ES): MH+ 378, M−H+ 376.

The compounds shown in Table 1 were prepared using methods analogous to that described in Example 1.

TABLE 1

| Example | Name | MH+/(M − H)+ |
|---|---|---|
| 2 | 6-(2,4-Difluorophenyl)-2-methyl-N-(2-methylbenzothiazol-5-yl)-nicotinamide | 396/394 |
| 3 | 6-(3,4-Difluorophenyl)-2-methyl-N-(2-methylbenzothiazol-5-yl)-nicotinamide | 396/394 |
| 4 | N-Benzothiazol-5-yl-6-(4-fluorophenyl)-2-methyl-nicotinamide | 364/362 |
| 5 | 6-(2,3-Difluorophenyl)-2-methyl-N-(2-methylbenzothiazol-5-yl)-nicotinamide | 396/394 |
| 6 | N-(2-Methylbenzothiazol-5-yl)-2-phenylpyrimidine-5-carboxamide | 347/345 |
| 7 | 4-Methyl-N-(2-methylbenzothiazol-5-yl)-2-phenylpyrimidine-5-carboxamide | 361/359 |
| 8 | 2-(4-Fluorophenyl)-4-methyl-N-(2-methylbenzothiazol-5-yl)pyrimidine-5-carboxamide | 379/377 |
| 9 | N-(2-Methylbenzothiazol-5-yl)-4-(6-methylpyridin-2-yl)benzamide | 360/358 |
| 10 | N-(2-Methylbenzothiazol-5-yl)-4-(1H-pyrazol-1-yl)benzamide | 335/333 |

EXAMPLE 11

N-(1-Benzimidazol-6-yl)-6-(4-fluorophenyl)-2-methyl-nicotinamide

6-Amino-1H-benzimidazole (27 mg, 0.20 mmol), 6-(4-fluorophenyl)-nicotinic acid (D3) (46 mg, 0.20 mmol), 1-(3-dimethyl-aminopropyl)-3-ethyl-carbodiimide hydrochloride (46 mg, 0.24 mmol) and 4-dimethylaminopyridine (12 mg, 0.10 mmol) in DCM (1.6 ml) were stirred at room temperature overnight. The reaction mixture was purified directly by column chromatography, eluting with a 0-5% MeOH/DCM gradient to give the title compound. MS(ES): MH+ 347, M−H+ 345.

The compounds shown in Table 2 were prepared using methods analogous to that described in Example 11.

TABLE 2

| Example | Name | MH+/(M − H)+ |
|---|---|---|
| 12 | 6-(4-Fluorophenyl)-2-methyl-N-(1-methyl-1H-benzimidazol-6-yl)-nicotinamide | 361/359 |
| 13 | N-indazol-6-yl-6-(4-fluorophenyl)-2-methyl-nicotinamide | 347/345 |
| 14 | N-Benzotriazol-5-yl-6-(4-fluorophenyl)-2-methyl-nicotinamide | 348/346 |

EXAMPLE 15

4-(4-Chlorophenyl)-N-(2-methylbenzothiazol-5-yl) cyclohexane-1-carboxamide

A suspension of 4-(4-chlorophenyl)-cyclohexane-1-carboxylic acid (100 mg, 0.42 mmol) in DCM (10 ml) was treated with catalytic DMF and oxalyl chloride (110 ul, 1.26 mmol) at 0° C. and the mixture was then stirred at room temp. for 1 h and at 45° C. for 2 h. The solvent and excess oxalyl chloride was removed in vacuo and the residue resuspended in DCM (5 ml). To this was added pyridine (35 ul, 0.42 mmol) and 5-amino-2-methylbenzothiazole (63 mg, 0.38 mmol) and the reaction stirred at room temp. overnight. MeOH (1 ml) was added and the mixture was washed with sat. aq. sodium bicarbonate solution and brine then dried (MgSO$_4$) and concentrated to give the title compound as an off-white solid (148 mg). $^1$H NMR (400 MHz, DMSO) δ (ppm): 8.37 (d, 1H), 7.96 (d, 1H), 7.63 (dd, 1H), 7.40 (d, 2H), 7.38 (d, 2H), 2.83 (s, 3H), 2.49-2.63 (m, 2H), 2.04 (m, 2H), 1.94 (m, 2H), 1.69 (m, 2H), 1.53 (m, 2H). MS(ES): MH+ 385/387, M−H+ 383/385.

EXAMPLE 16

4-(2-Fluorophenyl)-N-(2-methylbenzothiazol-5-yl)-1-piperazine carboxamide

To a stirred solution of 5-amino-2-methylbenzothiazole (100 mg, 0.61 mmol) and triethylamine (170 ul, 1.22 mmol) in DCM (5 ml) at 0° C. under an argon atmosphere was added triphosgene (60 mg, 0.2 mmol). The mixture was warmed to room temp. and stirred for 1 h. 4-(2-Fluorophenyl)piperazine (110 mg, 0.61 mmol) was added and the reaction was stirred at room temp. overnight. The solvent was removed in vacuo and the residue purified by chromatography eluting with a 0-100% EtOAc/petroleum ether gradient to give the title compound as a pale yellow solid (69 mg). $^1$H NMR (400 MHz, CDCl$_3$) δ (ppm): 7.82 (d, 1H), 7.71 (d, 1H), 7.53 (dd, 1H), 6.92-7.10 (m, 4H), 6.65 (s, 1H), 3.69 (m, 2H), 3.13 (m, 2H), 2.81 (s, 3H). MS(ES): MH+ 371, M−H+ 369.

EXAMPLE 17

4-(2,4-Difluorophenyl)-N-(2-methylbenzothiazol-5-yl)-1-piperazine carboxamide

Using the procedure outlined in Example 16, the title compound was prepared from 5-amino-2-methylbenzothiazole (100 mg, 0.61 mmol) and 4-(2,4-difluorophenyl)piperazine (121 mg, 0.61 mmol) as a pale yellow solid (95 mg). $^1$H NMR (400 MHz, CDCl$_3$) δ (ppm): 7.82 (d, 1H), 7.71 (d, 1H), 7.52 (dd, 1H), 6.76-6.94 (m, 3H), 6.74 (s, 1H), 3.68 (m, 2H), 3.04 (m, 2H), 2.80 (s, 3H).

EXAMPLE 18

6-(4-Fluorophenyl)-2-methyl-N-(1-methylindazol-5-yl)nicotinamide

Using the procedure outlined in Example 15, the title compound was prepared from 6-(4-fluorophenyl)nicotinic acid (D3) (100 mg, 0.43 mmol) and 5-amino-1-methylindazole (58 mg, 0.39 mmol) as a white solid (21 mg). MS (ES): MH+ 361, (M−H)− 359.

Pharmacological Data (a) In Vitro Assay

As referenced above, the compounds of the invention are Vanilloid receptor (VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129, 227-230).

Transfected astrocytoma 1321N1 cells, stably expressing human VR1, were seeded into FLIPR plates at 25,000 cells/well (96-well plate) and cultured overnight.

The cells were subsequently loaded in medium containing 4 μM Fluo-3 AM (Molecular Probes) for 2 hours, at room temperature, in the dark. The plates were then washed 4 times with Tyrode containing 1.5 mM calcium, without probenecid.

The cells were pre-incubated with compound or buffer control at room temperature for 30 minutes. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium concentration resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All the examples when tested by the above methodology gave a pKb>7.0.

(b) FCA-Induced Hyperalgesia in the Guinea Pig

100 μl of 1 mg/ml FCA was injected intraplantar into the left paw of 4 groups of 8 male Dunkin Hartley guinea-pigs (batch: 6282434, average weight 340 g). 24 hours later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Examples 1, 2, 3, 4, 5 and 16 were tested in this model and shown to be active.

The invention claimed is:

1. A compound represented by the following structure:

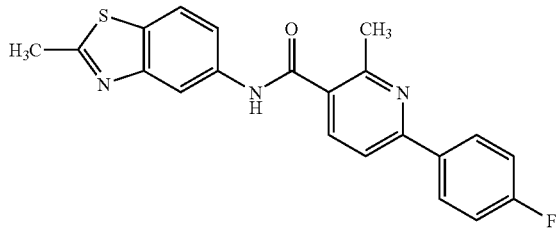

or a pharmaceutically acceptable salt thereof.

2. A pharmaceutical composition comprising the compound of claim 1 or a pharmaceutically acceptable salt thereof and a pharmaceutically acceptable carrier or excipient.

* * * * *